United States Patent [19]

Iseri et al.

[11] Patent Number: 6,077,418
[45] Date of Patent: Jun. 20, 2000

[54] CORROSION MONITORING

[75] Inventors: Hajime Iseri; Kuniyuki Takahashi; Yutaka Yoneda, all of Tokyo, Japan

[73] Assignee: Kurita Water Industries Ltd., Tokyo, Japan

[21] Appl. No.: 09/166,548

[22] Filed: Oct. 5, 1998

[30] Foreign Application Priority Data

Oct. 15, 1997 [JP] Japan .................................. 9-282035

[51] Int. Cl.[7] .................................................. G01N 17/04
[52] U.S. Cl. .................. 205/775.5; 205/776; 205/776.5; 205/777; 204/404; 204/408; 73/61.2; 73/86; 324/71.2; 324/700
[58] Field of Search .................................... 205/776, 777, 205/775.5, 776.5; 204/404, 408; 324/700, 71.2; 73/61.2, 86

[56] References Cited

U.S. PATENT DOCUMENTS

| | | | |
|---|---|---|---|
| 4,098,662 | 7/1978 | Schell et al. | 204/195 C |
| 4,121,088 | 10/1978 | Doremus et al. | 219/201 |
| 4,142,402 | 3/1979 | Mattioli et al. | 73/61.2 |
| 4,683,035 | 7/1987 | Hunt et al. | 204/404 |
| 4,686,854 | 8/1987 | Herman | 73/86 |
| 4,839,580 | 6/1989 | Moore et al. | 324/65 R |
| 5,854,557 | 12/1998 | Tiefnig | 205/777 |
| 5,888,374 | 3/1999 | Pope et al. | 205/777 |

OTHER PUBLICATIONS

Patent Abstracts of Japan, P–1706, p. 58, JP5–322831A(Kurita Water Ind Ltd), Dec. 7, 1993.

Patent Abstracts of Japan, JP11–44633A (Kurita Water Ind Ltd) Feb. 16, 1999.

*Primary Examiner*—Bruce F. Bell
*Attorney, Agent, or Firm*—Kanesaka & Takeuchi

[57] ABSTRACT

Corrosion of a metal member under heat transfer condition is monitored by using a test coupon made of the same material as that of the metal member. The test coupon may have a welded portion and a crevice. One substantial surface of the test coupon is heated by a sheet shaped heating element, and at least one portion of the other surface of the test coupon is contacted with the corrosive fluid. After detecting a status of corrosion of the test coupon, the corrosion of the metal member is monitored based on the results of the detection. In case a counter electrode or reference electrode is used, the electrode is immersed in the corrosive fluid, and electrical signals between the test coupon and the electrode are measured. Then, the corrosion of the metal member is monitored.

14 Claims, 8 Drawing Sheets

CORROSION MONITORING

FIELD OF THE INVENTION

The present invention relates to a method, a test coupon, and an apparatus for monitoring corrosion of a metal member used in a chemical plant or the like and, particularly, to a method and an apparatus for monitoring corrosion of the metal members under heat transfer conditions. More particularly, the present invention relates to a method and an apparatus for monitoring corrosion of the metal member by preparing a test coupon of the same or similar material as the metal member, and measuring extent of corrosion of the test coupon.

The present invention also relates to a test coupon for monitoring corrosion of a metal member such as a metallic heat exchanger tube in contact with water and to a corrosion monitoring method and apparatus using this test coupon. In detail, the present invention relates to a metallic test coupon having a welded portion, a crevice or gap, and a heat conductive portion is which brought in contact with water and to a corrosion monitoring method and apparatus which can actualize quick and precise prediction of corrosion of a metal member such as a metallic heat exchanger tube.

DESCRIPTION OF PRIOR ART

In a chemical plant, metal members of different materials and configurations are used as its structural members. Corrosion of these metal members finally brings about a penetration accident that occurs a serious problem such as shutdown of the plant, contamination to products, or the like. Techniques are demanded for measuring corrosion reaction and/or rate on structural members of a chemical plant, and various methods for measuring the corrosion reaction and/or rate including the followings have been tested.

i) JPA 5-322831 ii) U.S. Pat. 4,098,662 (Jul. 4, 1978)

iii) U.S. Pat. 4,686,854 (Aug. 18, 1987)

Disclosed in the above i) is a method for monitoring pitting corrosion on actual pipelines by measuring the corrosion potential.

The corrosion rate of metal changes according to temperature condition in such a manner that the corrosion rate of metal in contact with liquid tends to increase as the temperature increases. Examples of metal members, of which temperature increases, as structural members of a chemical plant, are a heat exchanger, a piping and a tank through which heated liquid passes, and so on. Disclosed in the above ii), iii) is an assembly for monitoring corrosion in a fluid system under heat transfer conditions which includes a tube-like electrode and an electric heater within the electrode.

The above i) through iii) have the following problems.

In the method of i), the same metallic material as used in an actual plant may be used, but, heating and heat transferring are not conducted. Therefore, it is difficult to monitor corrosion on heat transferring portions which are most easy to corrode in the actual plant. Since surface finishing is conducted, it is difficult to provide precise monitoring because the condition of surface is different from that of the actual plant. The monitoring assemblies of ii) and iii) are complex and have a danger of overheating in case of failure of heating control portion because of using a temperature sensor such as thermocouple. The utilization of the assembly in an actual plant may be limited.

The method disclosed in iii) is preparing heat transfer conditions by inserting the electric heater within the tube so that it requires a device for flowing liquid out of the tube, thereby increasing cost for manufacturing the device. There is also a problem of requiring an additional mounting work. There is still a problem that the metal piece for corrosion monitoring is limited to be of tube configuration and that the evaluation is made only about the outer surface of the tube.

In general, corrosion resistant metals such as stainless steel are passivated in fresh water, for example, in a cooling water system and they are known as corrosion resistant materials. However, as there is a structural crevice or an accretion crevice produced by fouling, corrosive ions such as chloride ions should be condensed so that there are possibilities of producing localized corrosion such as crevice corrosion and pitting corrosion. In this condition, when tensile stress is applied, there is further possibilities of stress corrosion cracking with the crevice corrosion and pitting corrosion as starting points ("Zairyo-to-Kankyo" 41 (1), 56, 1992 by Masahiro Nakahara). It is known that such stress corrosion cracking is apt to occur under high temperature conditions when the chloride content is constant (Journal of Japanese Petroleum Institute, 13,555, 1970 by Tomoyoshi Nishino, Mamoru Fujisaki).

Conventionally, one of known methods for evaluating stress corrosion cracking of corrosion resistant metals such as stainless steel comprises steps of immersing a test coupon, which is made up of two metal pieces joined by welding, into test water for a long period of time and, after that, observing the status of corrosion at portions surrounding the welded portion ("Zairyo-to-Kankyo" 43 (3), 126, 1994 by Toshio Adachi).

As cracking or penetration is caused in a pipe materials used, for example, in a heat exchanger by the progress of localized corrosion, it leads to a serious problem such as shutdown of the plant. Therefore, monitoring technique for predicting the generation of corrosion is important. As one of conventional methods for monitoring (observing or predicting) corrosion of metal, a method for monitoring the corrosion potential of the metal in a system where the metal and water are in contact with each other is known (JPA 5-98476).

In general, conventional corrosion monitoring is conducted by immersing a plate-like test coupon in a water system to be monitored. However, the test coupon has a uniform metal surface and neither a structural crevice where crevice corrosion and pitting corrosion are apt to occur nor a portion under tensile stress required for cracking is applied. There is a problem that the test coupon has low corrosion sensitivity for localized corrosion such as crevice corrosion and stress corrosion cracking.

As another one of conventional methods, there is a method in which variation in corrosion potential of a test coupon or tube during flowing water in a monitored system is monitored on the basis of a reference electrode. In this method, the water temperature about the test coupon is often lower than that of a heat conductive portion where local corrosion of corrosion resistant metal is apt to occur, for example, in an actual heat exchanger. This means that the evaluation is not conducted in the environment that corrosion problem is apt to occur.

OBJECT AND SUMMARY OF THE INVENTION

It is an object of the present invention to provide a method and apparatus of corrosion monitoring which allows easy monitoring (observation) of corrosion of a member in an actual plant under heat transfer conditions.

It is an object of the present invention to actualize the monitoring under conditions simulating the environment that corrosion problem is apt to occur in an actual plant.

A corrosion monitoring method of a first aspect is for monitoring corrosion of a metal member under heat transfer condition which corrodes during contact with corrosive fluid. The method comprises steps of: heating one surface of a test coupon made of the same material as that of the metal member by a sheet-like heating element; bringing at least one portion of the other surface of the test coupon into contact with the corrosive fluid; detecting extent of corrosion of the test coupon; and monitoring the corrosion of the metal member based on the results of the detecting.

A corrosion monitoring method of a second aspect is for monitoring corrosion of a metal member under heat transfer condition which corrodes during contact with corrosive fluid. The method comprises steps of: immersing a counter electrode or a reference electrode in the corrosive fluid, heating one surface of a test coupon made of the same material as that of the metal member by a sheet-like heating element; bringing at least one portion of the other surface of the test coupon into contact with the corrosive fluid; measuring electrical signals between the test coupon and the counter electrode or the reference electrode; and monitoring the corrosion of the metal member based on the results of the measurement.

A corrosion monitoring apparatus of a third aspect is for monitoring corrosion of a metal member under heat transfer condition which corrodes during contact with corrosive fluid. The apparatus comprises: a test coupon made of the same material as that of the metal member; a sheet-like heating element for heating one surface of the test coupon; and a detecting means for detecting the status of corrosion of the test coupon when at least a portion of the other surface of the test coupon is brought in contact with the corrosive fluid.

A corrosion monitoring apparatus of a fourth aspect is for monitoring corrosion of a metal member under heat transfer condition which corrodes in case where it is in contact with corrosive fluid. The apparatus comprises: a counter electrode or a reference electrode to be immersed into the corrosive fluid; a test coupon made of the same material as that of the metal member; a sheet-like heating element for heating one surface of the test coupon; and a measuring means for measuring electrical signals between the test coupon and the counter electrode or the reference electrode when at least a portion of the other surface of the test coupon is brought in contact with the corrosive fluid.

The heating element may be controlled by a temperature control means.

According to the methods and apparatuses of the present invention, the test coupon corrodes in the same conditions as that where the metal member is positioned in an actual plant and the extent of corrosion of the test coupon is directly measured, thereby achieving precise monitoring of corrosion of the metal member in the actual plant. The test coupon may be positioned under the same heat transfer conditions as the actual member, thereby actualizing quite -precise monitoring of corrosion of the actual member.

The present invention provides also a test coupon for corrosion monitoring of the metal member. The test coupon is made of the same material as that of the metal member, and has a welded portion, a crevice, and a heat transfer portion.

An embodiment of the test coupon comprises a plurality of (including two) metal pieces which are put on each other, and are partially jointed by spot welding to have spaces therebetween at portions other than the spot-welded portion.

Since the monitoring method and apparatus of the present invention employs such a test coupon having a welded portion, a crevice, and a heat transfer portion and variation in corrosion potential of the test coupon is monitored, thereby precisely monitoring local corrosion causing a corrosion problem of a metal member in an actual plant.

In the present invention, a sheet-like heating element is preferably attached to one side of the test coupon. The monitoring is conducted with heating the test coupon by the sheet-like heating element, thereby enabling local corrosion at high-temperature portions in the actual plant to be precisely monitored.

BRIEF DESCRIPTION OF THE DRAWINGS

FIGS. 1a, 1b are structural views of a test coupon for corrosion monitoring, wherein

FIGS. 2a, 2b are structural views of a test coupon for corrosion monitoring, wherein

FIGS. 3a, 3b are structural views of a test coupon for corrosion monitoring, wherein

FIGS. 4a, 4b, 4c are structural views of a test coupon for corrosion monitoring, wherein FIG. 4c is a sectional view taken along a line IVC—IVC of FIG. 4a;

FIGS. 5a, 5b, 5c, 5d are structural views of a test coupon for corrosion monitoring.

PREFERRED EMBODIMENTS

Hereinafter, embodiments will be described in detail with reference to drawings.

Figure 1A:
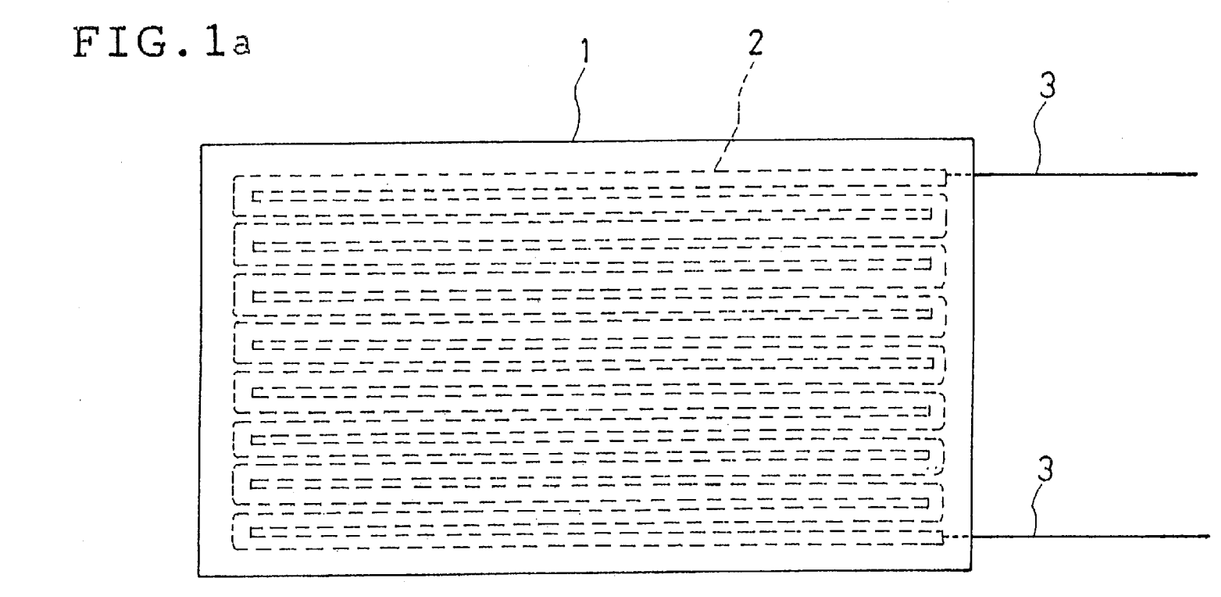
FIG. 1a is a plan view thereof and FIG. 1b is a side view thereof.
Figure 1B:
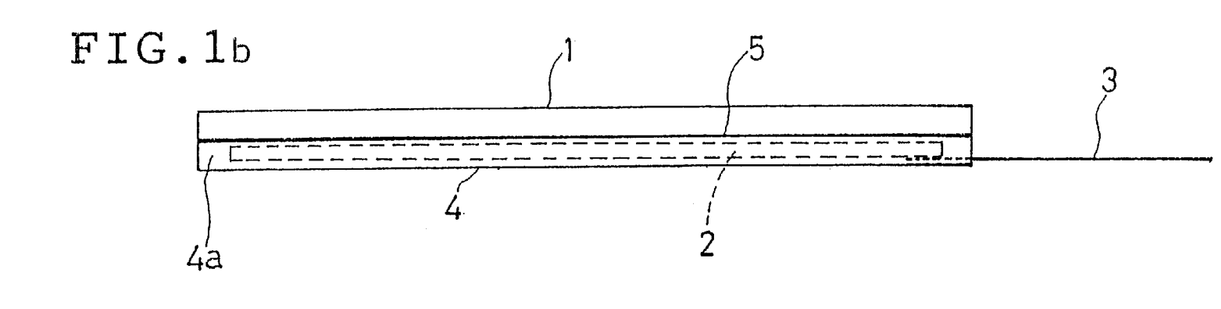

Embodiment of FIGS. 1a, 1b

FIG. 1a is a plane view of a test coupon to be used in a monitoring method according to the embodiment and FIG. 1b is a side view thereof.

A plate-like test coupon 1 is made of the same material as a metal member of an actual plant. The test coupon 1 is provided with a sheet-like heating element 4 which is bonded to the entire rear surface of the test coupon 1 by adhesives 5. The sheet-like heating element 4 is a plate comprising a heating resistor 2 made of thin metallic foil which is arranged in zigzag shape and an insulating synthetic resin 4a wherein the resistor 2 is molded in the synthetic resin 4a. Ends of two coated lead wires 3 are also molded in the synthetic resin 4a. The cores (not shown) of the coated lead wires 3 extend still outside of coated portions and to be connected to both terminals of the heating resistor 2, respectively.

The test coupon 1 is brought in contact with corrosive fluid in the actual plant and the current to the test coupon 1 is controlled in such a manner that the test coupon 1 is subjected to the same heat transfer conditions as that of the metal member as a monitoring object in the actual plant.

While the test coupon 1 is kept in the aforementioned conditions, the status of corrosion of the test coupon 1 is continuously or intermittently measured. Based on the results of the measurement, the member in the actual plant is monitored.

The method of measuring the status of corrosion of the test coupon may include visual observation and/or measurement of corrosion rate. The visual observation enables the determination whether the test coupon is corroding or not and the discrimination of the form of corrosion (for example, pitting corrosion, crevice corrosion, the form and shape of local corrosion such as stress corrosion cracking) as well as the rough measurement of corrosion rate.

When the test coupon is made of corrosive resistant metal such as stainless steel, copper, or copper alloy and is however corroding, the visual observation can measure the number and the depth of pits produced by pitting corrosion. For measuring the depth, a depth micrometer, a dial gauge, a microscope with focussing scale, or a surface roughness measuring equipment using laser microscope may be employed.

The corrosion rate can be measured based on a time period of contact of the test coupon with the corrosive fluid and variation in weight before and after the contact.

Concretely, the corrosion rate and the penetration can be obtained by the following equations (1), (2):

$$\text{Corrosion rate (mdd)} = (M_1 - M_2)/(S \cdot T) \quad (1)$$

wherein, $M_1$=weight (mg) of the test coupon before testing,
$M_2$=weight (mg) of the test coupon after testing,
S=surface area ($dm^2$) of the test coupon, and
T=Dates took for the testing, $$\text{Penetration (mm/y)} = (365 \cdot 10^{-4}/d) \cdot (M_1 - M_2)/(S \cdot T) \quad (2)$$

wherein, d=density ($g/cm^3$) of the test coupon,
$M_1$=weight (mg) of the test coupon before testing,
$M_2$=weight (mg) of the test coupon after testing,
S=surface area ($dm^2$) of the test coupon, and
T=Dates took for the testing.

Though one test coupon 1 made of one kind of material is attached to one surface of the heating resistor 2 coated with the insulating synthetic resin 4a in the embodiment shown in FIGS. 1a, 1b, a plurality of metallic materials (test coupons) of which surface area is smaller than the heating portion may be attached to the heating element. In case of using a plurality of test coupons, when these test coupons are conductors such as metal, the test coupons are usually attached such that these are not in contact with each other. However, these may be deliberately in contact with each other because the simulated galvanic corrosion can be produced even without using a special electric conductor such as a lead wire so as to actualize the measurement of the galvanic corrosion.

Though only one of surfaces of the heating element is provided with the test coupon in the embodiment shown in FIGS. 1a, 1b, both surfaces of the heating element may be provided with test coupons. In this case, the test coupons may be made of the same material or different materials. In also this case, there is no limitation on the number of test coupons as long as the test coupons are within the area of the heating element. Though the test coupon 1 is attached to the sheet-like heating element including the resistor 2 with the adhesives 5 in the embodiment shown in FIGS. 1a, 1b, the test coupon and the heating resistor may be molded integrally.

Adhesives having large heat transfer coefficient may be preferably used as the adhesives 5. However, by variation of heat transfer coefficient of the adhesives, the temperature of the test coupon can be varied even with the same heating element.

The surface of the test coupon may be partially coated by an insulating body as necessary. For example, when a metallic material cut from the actual plant is used as the test coupon and it is not desired that the cutting edges and portions damaged during the cutting affect the evaluation, these portions are coated by insulating body as necessary.

There is no particular limitation on the dimension and configuration of the sheet-like heating element. It is preferable that the dimension and configuration of the sheet-like heating element is designed to correspond to the dimension and configuration of the test coupon to which the sheet-like heating element is attached. When the sheet-like heating element has heat conductive portions on both surfaces thereof, the test coupons may be attached to both surfaces of the sheet-like heating element. When the test coupon is attached to only one surface of such a sheet-like heating element, heat insulating material may be attached to the other surface, to which no test coupon is attached, to reduce heat emission from scattering from the surface to which no test coupon is attached. The heat conductive surface as the sheet-like heating element can be made of flexible material or formed previously in a desired configuration so that it can be attached even to the test coupon having a curved surface.

The test coupon may be positioned directly in a piping or tank as corrosive environment of the actual plant. When fluid is the cause of corrosion, the fluid is taken into a separate tank and the apparatus of the present invention may be immersed in the fluid.

According to the present invention, even when the temperature of the corrosive environment is low, the evaluation on the heat transfer surface can be conducted. This means that the corrosion evaluation can be carried out at a relatively safe place apart from a high-temperature plant equipment or system so that the corrosion monitoring can be carried out safely.

The test coupon may be used for corrosion evaluation under heat transfer conditions when corrosive materials are sampled and carried to another place or for corrosion evaluation under heat transfer conditions that is simulated corrosion situation in a laboratory.

Figure 2A:
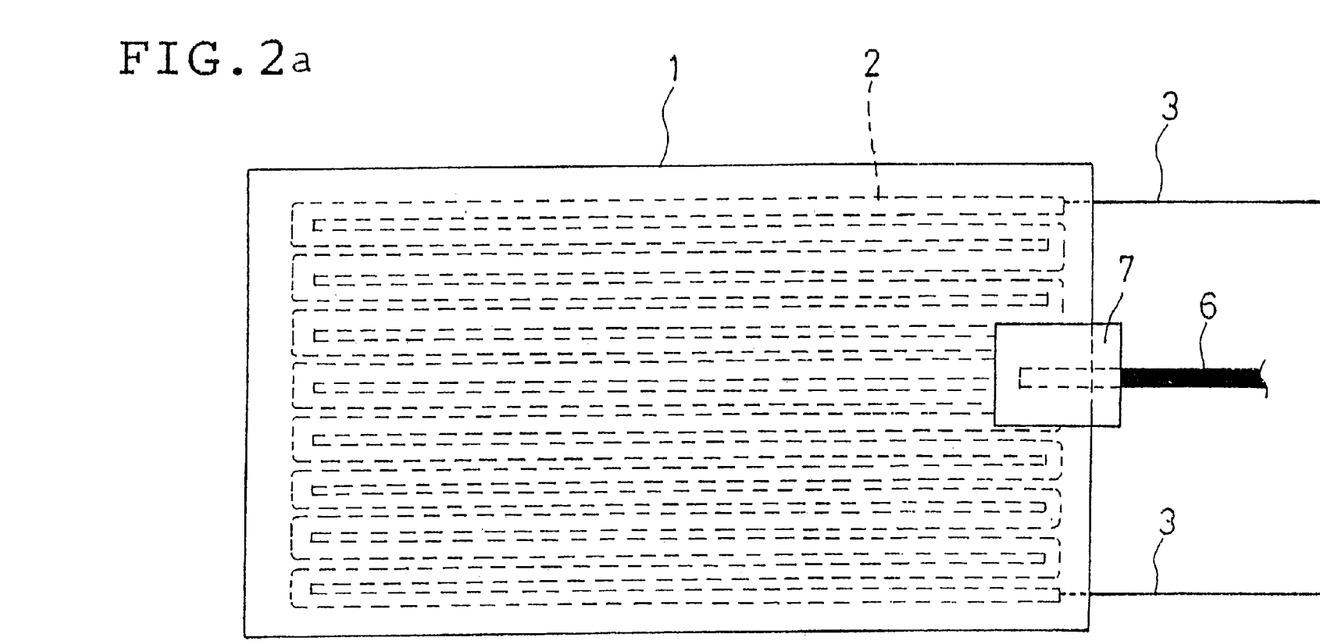
FIG. 2a is a plan view thereof and FIG. 2b is a side view thereof.
Figure 2B:
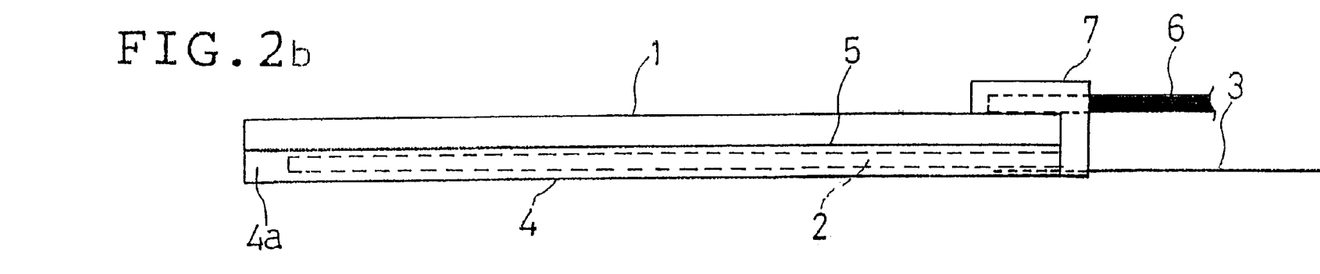

Embodiment of FIGS. 2a, 2b

FIGS. 2a, 2b are a plane view and a side view showing a test coupon which can actualize the corrosion monitoring of the test coupon by electrochemical signals. The test coupon of FIGS. 2a, 2b is the same as the test coupon 1 shown in FIGS. 1a, 1b, but having a coated lead wire 6. An end of the coated lead wire 6 is fixed to the test coupon 1 by corrosive resistant resin mold 7. The core of the coated lead wire 6 is connected to the test coupon 1. The other compositions are the same as that shown in FIGS. 1a, 1b.

The test coupon of FIGS. 2a, 2b is brought in contact with corrosive fluid in the same manner as that of FIGS. 1a, 1b. In this embodiment, corrosion potential between the test coupon and a reference electrode (not shown) can be measured through the coated lead wire 6. The potential measurement may be made by a potentiometer, a digital multimeter, tester, or a computer utilizing an A/D converter for voltage input. Examples of the reference electrodes include Ag/AgCl/sat. KCl electrode, SCE electrode, Cu/CuSO$_4$ electrode, and Hg/Hg$_2$SO$_4$ electrode.

As a general rule, the higher the corrosion potential of metallic material, the higher the possibility of pitting corrosion and/or crevice corrosion. The measurement of the corrosion potential is one of effective monitoring methods for predicting occurrence of corrosion of metallic material to be monitored by knowing the corrosion tendency of the metallic material. The corrosion monitoring can be more effectively conducted by using a data logging equipment such as a computer for continuously measuring for the corrosion monitoring.

In the monitoring method using the test coupon of FIGS. 2a, 2b, the test coupon 1 is applied with micro current or micro potential variation by polarizing between the test coupon 1 and the reference electrode (not shown) separately disposed in the corrosive fluid. By measuring the resultant potential response or current response, the polarization resistance of the metallic material can be measured. The polarization resistance can be converted to the corrosion rate or penetration by the following equations (4), (5) based on the following Stem's equation (3):

$$R_p = (\partial \Delta E/\partial I)\Delta E \to 0 \quad (3)$$

Wherein, $R_p$=polarization resistance ($\Omega$cm$^2$) per unit area, $\Delta E$=polarization voltage (V) from corrosion potential, and I=current density (A/cm$^2$) at $\Delta E$, $$\text{Corrosion rate (mdd)} = 89500 \cdot M \cdot K/(n \cdot R_p) \quad (4)$$

wherein, M=unit atomic weight (mg) of the test coupon,

K=conversion factor (V), n=number of electrons of corrosion reaction on the test coupon, and $R_p$=polarization resistance ($\Omega$cm$^2$) per unit area, $$\text{Penetration (mm/y)} = 3270 \cdot M \cdot K/(d \cdot n \cdot R_p) \quad (5)$$

wherein, M=unit mass (mg) of the test coupon,

K=conversion factor (V),

D=density (g/cm$^3$) of the test coupon, n=number of electrons of corrosion reaction on the test coupon, and $R_p$=polarization resistance ($\Omega$cm$^2$) per unit area, The polarization measurement can be conducted by means of a three-electrode method using three electrodes: the test coupon as a working electrode; the reference electrode, the counter electrode or a two-electrode method in which the counter electrode also functions as the reference electrode. The current to be used is preferably direct current or low-frequency alternating current and the measurement is preferably conducted under constant current or constant potential conditions.

When the corrosion rate and the penetration are calculated based on the polarization resistance, it is preferable that the liquid resistance is measured and subtracted from measurement of the apparent polarization resistance so as to obtain actual polarization measurement, and this measurement is used for the calculations of the corrosion rate and the penetration. This compensation by the liquid resistance measurement is effective particularly when the conductivity of the corrosive fluid, in which the metallic material to be monitored is immersed, is small.

As an apparatus for the polarization measurement, a power supply such as a constant current device or constant potential device, a combination of ammeter and high input impedance voltmeter or an apparatus having the same functions is employed. The corrosion rate measurement by the polarization measurement can measure the corrosion rate at the moment of measurement. That is, it enables on-line corrosion monitoring. Furthermore, by using a data logging equipment such as a computer, the continuous measurement that the corrosion rate is measured continuously on line is actualized and the corrosion monitoring on a heat transfer surface, where a corrosion accident is apt to occur, is also actualized.

When the reference electrode and the counter electrode are disposed in a system to be monitored, electrochemical corrosion measurements besides the polarization resistance measurement, i.e. anodic polarization measurement, cathodic polarization measurement, alternating current impedance measurement, and the like, are actualized under heat transfer conditions. These electrochemical measurements allow the estimation of corrosion reaction mechanism, the measurement of pitting corrosion potential, the measurement of crevice corrosion re-passivation potential, and the like, and allow the measurement of corrosion tendency of metal material and comparison of corrosion resistance to be conducted under heat transfer conditions.

By using test coupons of two kinds, the measurement of galvanic corrosion can be conducted under heat transfer conditions. For example, by connecting two test coupons made of different kinds of metals through a lead wire, the monitoring of galvanic corrosion can be conducted under heat transfer conditions. In this case, corrosion measuring method is capable of measuring current flowing through a shorted lead wire, i.e. so-called galvanic current, of measuring potential in case of conductor shorted (connected), and measuring respective corrosion potentials in case of lead wire disconnected.

Figure 3A:
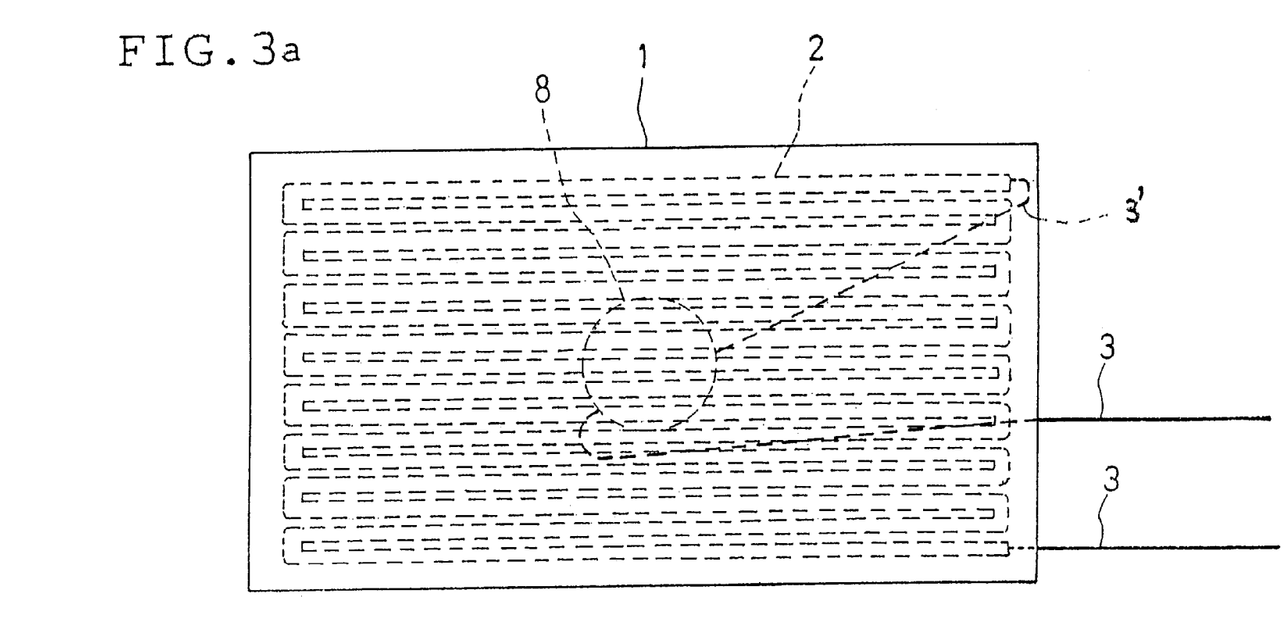
FIG. 3a is a plan view thereof and FIG. 3b is a side view thereof.
Figure 3B:
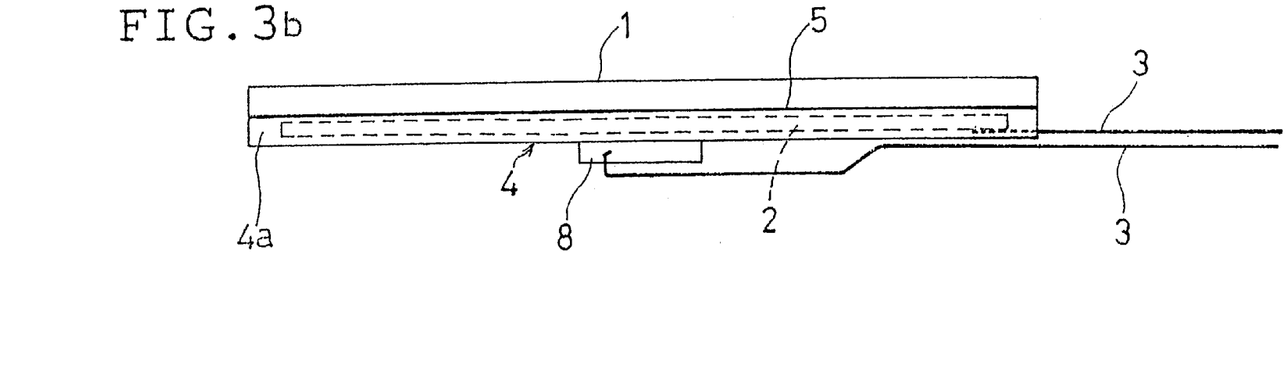

Embodiment of FIGS. 3a, 3b

The abnormal heating can be prevented by controlling the current to the heating resistor 2 of the sheet-like heating element 4 or by thermal emission to the outside of a system to be monitored when the test coupon 1 of FIGS. 1a, 1b, 2a and 2b is disposed in the system. However, a corrosion monitoring apparatus including a temperature control mechanism for the heating element is more preferable as shown in FIGS. 3a and 3b.

In FIGS. 3a, 3b, a disc-like bimetal thermostat 8 which is coated with an insulating body is attached to the heating element to control the temperature. One of coated lead wires 3 is connected to one of terminals of the heating resistor 2 and the other coated lead wire 3 is connected to the other terminal of the heating resistor 2 through the thermostat 8 and a coated lead wire 3'.

Instead of the bimetal thermostat, a liquid expansion thermostat may be employed. Instead of the thermostat, a temperature sensor such as a thermocouple and a thermoregulator may be employed.

Though the bimetal thermostat 8 is used in FIGS. 3a, 3b, a temperature sensor and a thermoregulator may be employed. The temperature sensor may be attached to a surface of the test coupon opposite to the bonding surface between the sheet-like heating element and the test coupon and may be coated with the insulating body. When the temperature sensor is thin, for example, when a thin thermocouple is used as the temperature sensor, the temperature sensor may be positioned the inside insulating body between the heating element and the test coupon.

Though the heating element is in a thin-foil-like configuration in FIGS. 1a, 1b, 3a, 3b, it may be in a strip-like, wire-like, or sheet-like configuration. In any of these configurations, the heating element has a sheet-like heating portion of uniform temperature. The material of the heating resistor may be a nickel alloy, carbon, or the like, and is not limited particularly. There is no particular limitation on the wiring pattern of the foil-like, strip-like, wire-like heating element. The heating element is preferably arranged so as to heat the test coupon entirely. The wiring pattern of the foil-like heating element may be formed by an etching method.

The insulating synthetic resin for coating the heating element may be any of resins, which do not deteriorate even in contact with the corrosive fluid. Examples include thermoplastic resins such as polyethylene and setting resins such as silicone resin. Adhesives employed as the adhesives 5 do not deteriorate even in contact with the corrosive fluid.

By coating the lead wires 3, 3', 6 with insulating material, the test coupon 1 can be directly disposed in electrolyte such as aqueous solution. The test coupon 1 is disposed in the system, where the corrosion monitoring is required, so that the test coupon 1 is bought into contact with the corrosive fluid. Then the test coupon 1 is brought in the same heat transfer conditions as that of a portion to be monitored. The corrosion monitoring is conducted in this condition. To improve the heat transferring from the heating element, a small heat conductive substance may be applied to the insulating body on the surface of the sheet-like heating element opposite to the test coupon side.

By varying the thickness of the insulating body disposed between the sheet-like heating element and the metallic material to be monitored, the temperature of the metallic material to be monitored can be changed only with one kind of sheet-like heating element. Instead of varying the thickness, by preparing insulating bodies having different heat coefficients, the temperature of metallic material to be monitored can be changed only with one kind of sheet-like heating element in the same manner. This is one of effective method when a heat conductive portion should be monitored at various temperatures for respective processes. When a heat conductive portion should be monitored at various temperatures for respective processes, the composition of the sheet-like heating element or electrical energy to be supplied may be varied.

Figure 4A:
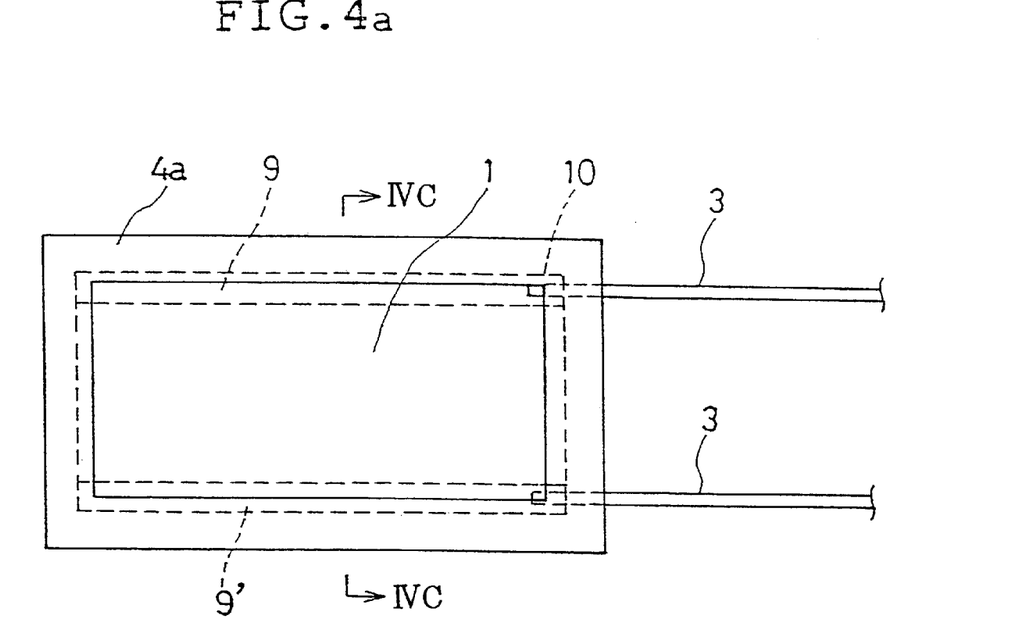
FIG. 4a is a plane view thereof.
Figure 4B:
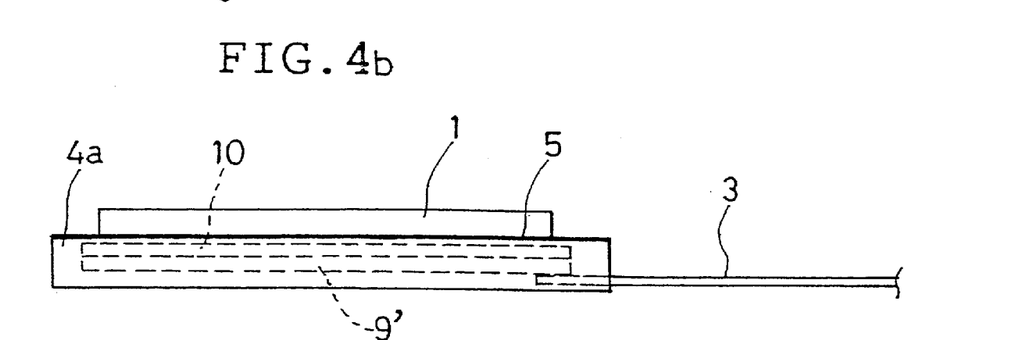
FIG. 4b is a side view thereof.
Figure 4C:
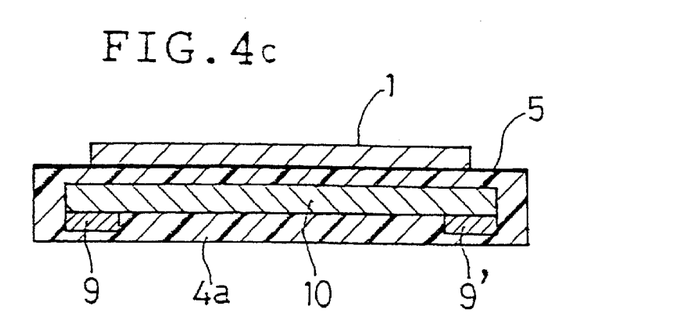
Figure 5A:
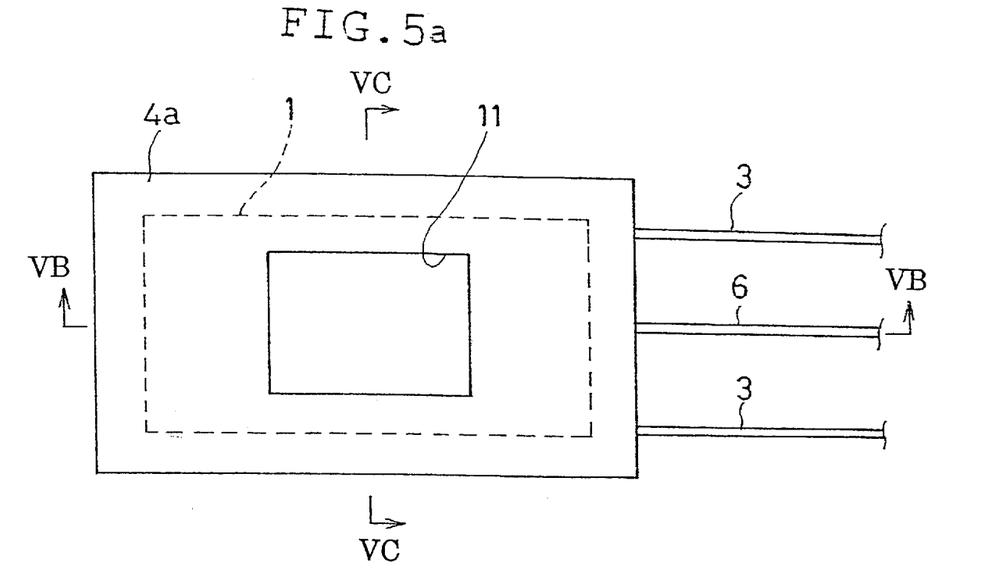
FIG. 5a is a plane view thereof.
Figure 5B:
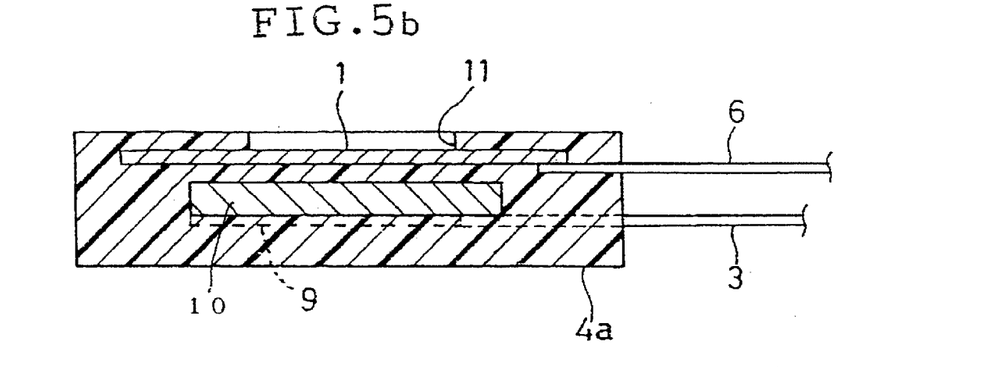
FIG. 5b is a sectional view taken along a line VB—VB of FIG. 5a, FIG. 5c is a sectional view taken along a line VC—VC of FIG. 5a, and FIG. 5d is a diagram of the pattern of a conductor.
Figure 5C:
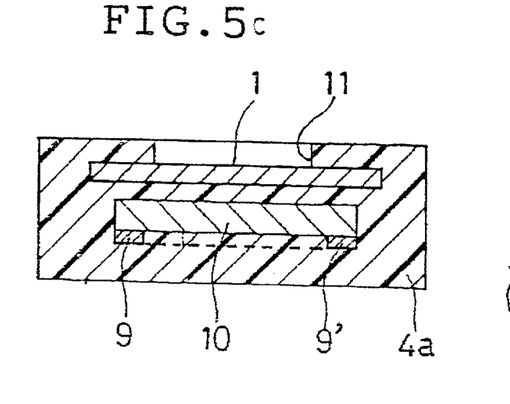
Figure 5D:
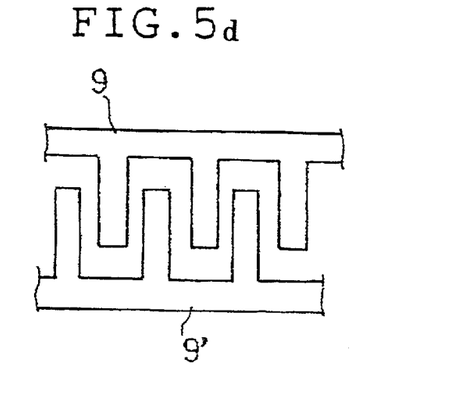

Embodiment of FIGS. 4a through 4c

In general, when a temperature sensor is positioned on an outer surface of a test coupon, the reliability is inferior because the temperature sensor detects only the temperature at a portion where the sensor is in contact with. In addition, in the temperature sensor failure, overheating occurs so that desired corrosion monitoring can not be obtained.

The test coupon of FIGS. 4a through 4c is provided with a PTC (Positive Temperature Coefficient) heater 10 in order to prevent such problems.

In FIGS. 4a through 4c, coated lead wires 3, 3' are connected to conductors 9, 9'. PTC heater 10 and the conductors 9, 9' are molded by insulating synthetic resin 4a. The test coupon 1 is bonded to the molded plate member at a portion confronting to the PTC heater 10 by adhesives 5.

The PTC heater has positive temperature characteristic as well known in the art. As current is applied to the PTC heater through the conductors 9, 9' disposed on both sides thereof, the PTC heater is heated to a predetermined temperature. Since the resistance of the PTC heater rapidly increases after exceeding Curie temperature, the PTC heater never exceed a predetermined temperature.

When the PTC heater is used as the heating element, both surface of the corrosion monitoring apparatus can be easily formed in flat shape or curved shape as compared to the case where an external temperature sensor is used as the embodiment shown in FIGS. 3a and 3b. Therefore, one or more metallic materials can be easily positioned on both surfaces of the corrosion monitoring apparatus.

Since the heating element itself has a temperature controlling mechanism, the utilization of the PTC heater as the heating element makes the structure simple and reduces the manufacturing cost. It is also advantageous because there is no danger of overheating that is caused in case of temperature sensor failure when the external temperature sensor is used. In addition, since the PTC heater has the temperature controlling mechanism through the entire heating element, the PTC heater can heat the test coupon uniformly as compared to the temperature control by the external temperature sensor.

Positive characteristic resistor components composing the PTC heater 10 include barium titanate added with traces of rare earth, mixture of thermoplastic resin and conductive material, mixture of organic compound having alkylene oxide as unit element and conductive material, and mixture of setting silicone rubber and conductive material.

The thermoplastic resins used in the mixture of thermoplastic resin and conductive material include polyethylene, polypropylene, polyvinyl chloride, polyethylene terephthalate, polyvinylidene chloride, fluorocarbon polymer, polyamide, and ethylene-vinyl acetate copolymer. The conductive materials include carbon particles, carbon beans, metal powder, carbon staples, and carbon whisker.

The organic compounds of alkylene oxide group used in the mixture of organic compound having alkylene oxide as unit element and conductive material as the positive characteristic resistor component include polyethylene glycol, polyethylene oxide, block copolymer of polyoxyethylene and polyoxypropylene (so-called Pluronic), polyoxyethylene alkyl ether, polyoxyethylene alkyl allyl ether, polyoxyethylene alkyl ester, polyoxyethylene alkyl amine, polyoxyethylene sorbitan fatty acid ester, trioxane, and crown ethers. The conductive materials include carbon particles, carbon beans, metal powder, carbon staples, and carbon whisker.

The setting silicone rubber used in the mixture of setting silicone rubber and conductive material include silicone rubber containing organopolysiloxane having at least three silicon atom bonding hydrolytic groups par molecule, silicone rubber containing organopolysiloxane having at least two silanol groups or two silicon atom bonding hydrolytic groups par molecule and organic silicone compound having at least, on average, two silicon atom bonding hydrolytic groups par molecule, and mixture of organopolysiloxane having at least two alkenyl groups bonded to silicone atom per molecule and organopolysiloxane having, on average, over two hydrogen atoms bonded to silicone atom as crosslinking agent in which platinum catalyst is added as curing agent. Examples of conductive materials include carbon particles, carbon beans, metal powder, carbon staples, and carbon whisker.

In the positive characteristic resistor components as mentioned above, Curie temperature can be varied by varying the ratio of compounds in the component. In the present invention, it is therefore required to suitably select a positive characteristic resistor component having temperature characteristics which can actualize desirable conditions.

Embodiment of FIGS. 5a through 5d

As shown in FIGS. 5a through 5d, a coated lead wire 6 is attached to a test coupon 1 of the same structure as that of FIGS. 4a through 4c. The corrosion monitoring is performed by applying voltage and/or applying micro current to the test coupon 1. In FIGS. 5a through 5d, the surrounding of the PTC heater 10 is molded with resin 4a. In case of performing electrochemical measurement, the area of a portion to be monitored is preferably not too large, for example, preferably 10 cm$^2$ or less. Therefore, the metallic material 1 to be monitored is coated with insulating synthetic resin 4a except a monitored portion (opening) 11. The conductors 9, 9' are each formed in a comb-like configuration, thereby heating uniformly entirely the PTC heater 10.

Though the test coupon 1 is formed in plate-like configuration in each of the embodiments mentioned above, the test coupon is not particularly limited on its configuration as long as having at least one flat surface or curved surface. Examples of configurations having a curved surface include bar-like, tubular, half-tubular, and cylindrical configurations.

Even an article comprising two plates welded to imitate a crevice for monitoring localized corrosion at the crevice may be employed as long as having at least one flat surface or curved surface.

The test coupon can be made of the same material as that used in various processes in the actual plant or of any material which is not used in the actual plant but is probably used. Pieces which were cut from various processing units and have been exposed to the corrosive environment of the actual plant may also be employed.

Though one test coupon is disposed for the PTC heater 10 in FIGS. 4a through 4c and 5a through 5c, two or more of test coupons may be disposed and, in this case, these may be disposed on both sides of the PTC heater 10.

According to the present invention, there is no limitation on the material and the configuration of the test coupon as long as having at least one flat surface or curved surface so that metal pieces of that various materials and various configurations can be employed such as test coupons cut from the actual plant. The correct corrosion monitoring can be performed under heat transfer conditions.

According to the present invention, the corrosion monitoring can be easily made even under heat transfer conditions so that the corrosion monitoring about many metallic materials can be conducted at the same time. In addition, the test coupon can be easily disposed in the corrosive environment of the actual plant, thereby actualizing the corrosion monitoring in the actual corrosive environment.

According to the present invention, the on-line corrosive measurement can be conducted under heat transfer conditions still without limitation of material. The present invention can be applied to a corrosion evaluation test in a laboratory, thereby favoring the corrosive evaluation test under heat transfer conditions.

There is no limitation on metallic material used for the test coupon of the present invention and the present invention can be particularly preferably applied for the corrosion monitoring of corrosion resistant metallic materials such as stainless steel, nickel, nickel alloy, titanium, titanium alloy, aluminum, aluminum alloy, copper, copper alloy, chromium, chromium alloy, molybdenum, molybdenum alloy, tungsten, tungsten alloy, and magnesium alloy.

Figure 7A:
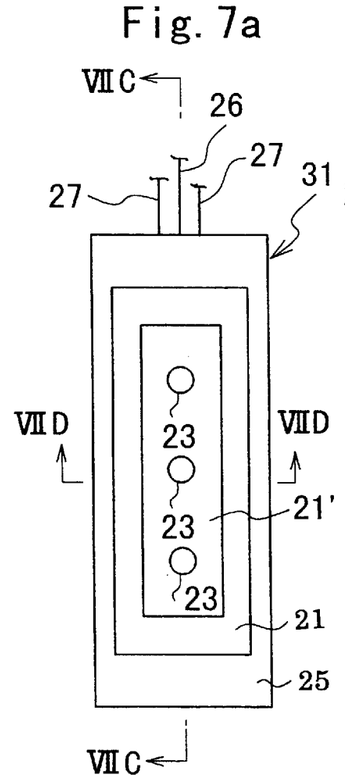
FIGS. 7a, 7b, 7c, 7d are structural views showing a test coupon of an example of the present invention.
Figure 7B:
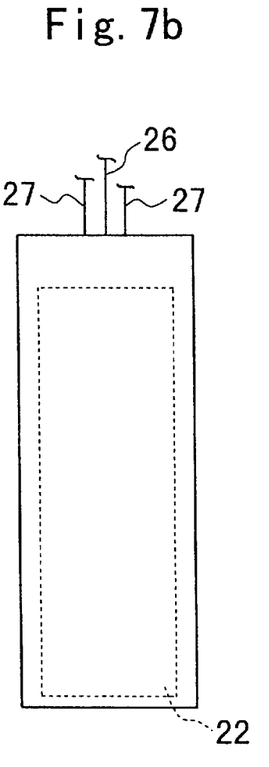
Figure 7C:
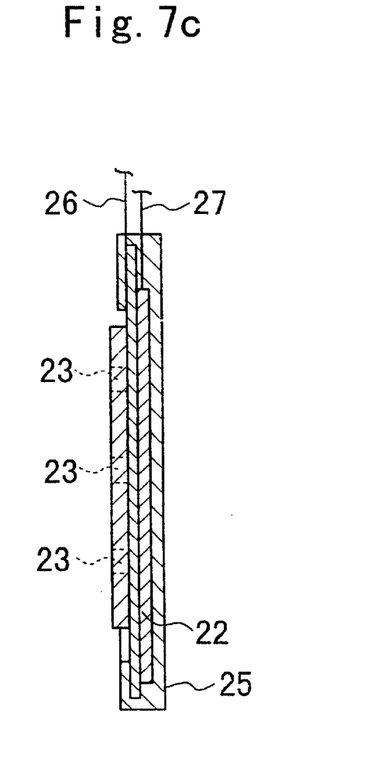
Figure 7D:
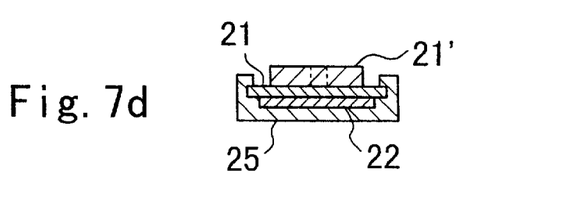

FIGS. 7a, 7b are a front view and a rear view showing a test coupon 31 according to an embodiment of the present invention, FIGS. 7c, 7d are sectional views taken along lines VIIC–VIIC and VIID–VIID, respectively.

Metal pieces 21, 21' made of stainless steel (SUS304 of Japanese Industrial Standard) are welded at spot welded portions 23 by spot welding. There are spaces between the metal pieces 21, 21' at portions other than the spot-welded portions 23. An end of a coated lead wire 26 for potential measurement is connected to the metal piece 21 by soft soldering or the like, and the connected portion is coated by insulating material (for example, silicone resin). A sheet-like heating element 22 is bonded to an outer surface of the metal piece 21 by adhesives. Connected to the sheet-like heating element 22 are coated lead wires 27 for continuity.

The sheet-like heating element 22 is a heating element composed of positive characteristic resistor component and coated by insulating material 25 (for example, silicone resin).

The dimension of the sheet-like heating element 22 is slightly smaller than the metal piece 21. The sheet-like heating element 22 is entirely sealed and the peripheral portion of the metal piece 21 positioned outside of the sheet-like heating element 22 is also sealed by the aforementioned insulating material 25. The insulating material 25 further covers the peripheral portion of the inner surface (the surface confronting the metal piece 21) of the metal piece 21 through the ends of the metal piece 21.

There is no limitation on configuration of two metal pieces which are bonded by welding as long as the pieces are made of the same material. It is preferable that the pieces are joined by welding after processing the surfaces thereof to have the same condition as that of monitored metal.

There is no particular limitation on the welding and thus spot welding may be employed. Such a test coupon, which has expulsion during the welding, should not be used. While there is no particular limitation on the number of welded portions for joining two metal pieces, the metal pieces are suitably joined at one to three portions. It is preferable that the surface area of the metal pieces except welded portions is wider than the area of the welded portions. Any subsequent treatment (stress relief) is not made around the welded portion after welding.

The welding condition can be changed corresponding to the corrosion rate of the system to be monitored and the corrosion sensitivity (residual stress, sensitivity, etc.) of the metal to be monitored, so the corrosion sensitivity of welded metal pieces with crevice therebetween, thereby actualizing the monitoring in quite similar condition as that of the actual plant.

In addition, the corrosion sensitivity can be controlled by sensitization.

The crevice between two metal pieces joined by welding is preferably set in such a manner that the width (a of FIG. 6) of a crevice opening is one tenth of the depth (b of FIG. 6) of the crevice or smaller.

Figure 6:
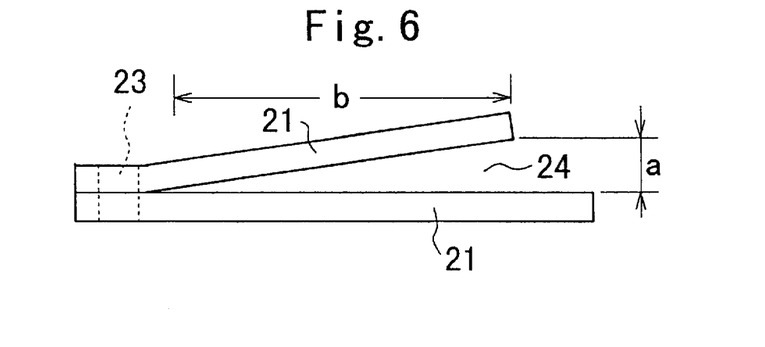
FIG. 6 is a schematic view illustrating the test coupon of the present invention.

FIG. 6 is a schematic side view showing an example of the test coupon of the present invention in which metal pieces 21, 21 are welded at a spot welding portion 23 and there is a crevice 24 between the metal pieces 21, 21.

By connecting coated lead wires to the test coupon, the potential can be measured through the coated lead wires. There is no a particular limitation on method for connecting the test coupon and the coated lead wires. Examples include a method of connecting the coated lead wires having a crimp-style terminal to the test coupon by a screw and a connecting method by soft soldering. The connecting portions between the test coupon and the coated lead wires are required to be coated with insulating resin for preventing the corrosion when immersed in a test liquid.

A sheet-like heating element is attached to the wider surface of outer surfaces of the welded metal pieces. When the areas of the outer surfaces of the two metal pieces are the same, the heating element is attached to any one of the pieces. The sheet-like heating element enables the uniform heating of the test coupon so that the environment of the heating conductive surface can be simulated.

The sheet-like heating element is not limited particularly. The sheet-like heating element is required to be bonded to the welded metal pieces with crevice therebetween in such a manner as to have no continuity between the metal pieces and the sheet-like heating element. As one of methods to achieve the above, the outer surface of the sheet-like heating element may be coated with insulating resin.

It is preferable that the test coupon is heated by the sheet-like heating element in such a manner that the temperature of the heat conductive surface becomes the same as that of the heat conductive surface of the metal to be monitored. It is therefore preferable that the sheet-like heating element is provided with a temperature control mechanism. As the temperature control mechanism a liquid expansion thermostat, a bimetal thermostat, or a control mechanism using a thermocouple temperature sensor may be employed.

By using, as the sheet-like heating element, a PTC heater having characteristics that the electrical resistance changes rapidly relative to temperature change, i.e. positive characteristics, the apparatus can be manufactured more simply because the heating element itself has function of controlling temperature. When the PTC heater is employed as the heating element, no external temperature sensor is required, so there is no danger of overheating in case of failure. In general, it requires less electrical energy as compared to temperature control by an external temperature sensor, thereby favoring the energy conservation.

Examples as positive characteristic resistor components composing the PTC heater 10 include barium titanate added with traces of rare earth, mixture of thermoplastic resin and conductive material, mixture of organic compound having alkylene oxide as unit element and conductive material, and mixture of setting silicone rubber and conductive material.

Among them, examples of thermoplastic resins used in the mixture of thermoplastic resin and conductive material include polyethylene, polypropylene, polyvinyl chloride, polyethylene terephthalate, polyvinylidene chloride, fluorocarbon polymer, polyamide, and ethylene-vinyl acetate copolymer. Examples of conductive materials include carbon particles, carbon beans, metal powder, carbon staples, and carbon whisker.

Examples of organic compounds of alkylene oxide group used in the mixture of organic compound having alkylene oxide as unit element and conductive material as the positive characteristic resistor component include polyethylene glycol, polyethylene oxide, block copolymer of polyoxyethylene and polyoxypropylene (so-called Pluronic), polyoxyethylene alkyl ether, polyoxyethylene alkyl allyl ether, polyoxyethylene alkyl ester, polyoxyethylene alkyl amine, polyoxyethylene sorbitan fatty acid ester, trioxane, and crown ethers. Examples of conductive materials include carbon particles, carbon beans, metal powder, carbon staples, and carbon whisker.

Examples of setting silicone rubber used in the mixture of setting silicone rubber and conductive material include silicone rubber containing organopolysiloxane having at least three silicon atom bonding hydrolytic groups par molecule, silicone rubber containing organopolysiloxane having at least two silanol groups or two silicon atom bonding hydrolytic groups par molecule and organic silicone compound having at least, on average, two silicon atom bonding hydrolytic groups par molecule, and mixture of organopolysiloxane having at least two alkenyl groups bonded to silicon atom per molecule and organopolysiloxane having, on average, over two hydrogen atoms bonded to silicon atom as crosslinking agent in which platinum catalyst is added as curing agent. Examples of conductive materials include carbon particles, carbon beans, metal powder, carbon staples, and carbon whisker.

In the positive characteristic resistor components as mentioned above, Curie temperature can be varied by varying the ratio of compounds in the component. In the present invention, it is therefore required to suitably select a positive characteristic resistor component having temperature characteristics which can actualize desirable heat transfer conditions.

There is no particular limitation on the dimension and configuration of the sheet-like heating element. It is preferable that the dimension and configuration of the sheet-like heating element are designed to correspond the dimension and configuration of the test coupon to which the sheet-like heating element is attached. When the sheet-like heating element has heat conductive portions on both surfaces thereof, the test coupons may be attached to both surfaces of the sheet-like heating element. When the test coupon is attached to only one surface of such a sheet-like heating element, heat insulating material may be attached to the other surface, to which no test coupon is attached, to reduce heat emission from scattering from the surface to which no test coupon is attached. The heat conductive surface as the sheet-like heating element can be made of flexible material or formed previously in a desired configuration so that it can be attached even to the test coupon having a curved surface.

There is no particular limitation on the method of bonding the test coupon and the sheet-like heating element, so adhesives or a pressure sensitive adhesive double coated tape may be employed. However, it is necessary to use adhesive material having such characteristics as not to be affected by heat emitted from the sheet-like heating element.

The test coupon and the sheet-like heating element are required to be protected to block water from flowing into the space between the test coupon and the sheet-like heating element. One of examples of measures is a method of sealing the space between the metallic test coupon and the sheet-like heating element by insulating material. Other portions in addition to the space between the metallic test coupon and the sheet-like heating element, i.e. other portions except the portion to be monitored, can be also sealed.

A test coupon holder made of insulating material may be used which has an opening to bring only the monitored portion in contact with the test water and which can cover the test coupon not to bring the other portions in contact with the test water. In this case, it is necessary to eliminate spaces between the holder and the heat conductive surface (metal surface) along the opening of the holder in order to prevent the crevice corrosion around this portion.

The method and apparatus for corrosion monitoring of the present invention comprises bringing the aforementioned test coupon of the present invention in contact with water (sometimes referred to test water) of the system to be monitored and measuring variation in corrosion potential of the test coupon.

Concretely, for example, the aforementioned test coupon and the reference electrode (standard electrode) are immersed into the test water and potential difference between the test coupon and the reference electrode is measured with time. In this case, a coated lead wire must be connected to the test coupon and the potential difference is measured through the coated lead wire.

The potential measurement may be made by a potentiometer, a digital multimeter, tester, or a computer utilizing an A/D converter for voltage input. Examples of the reference electrodes include Ag/AgCl/sat. KCl electrode, SCE electrode, Cu/CuSO$_4$ electrode, and Hg/Hg$_2$SO$_4$ electrode.

There is no particular limitation on the method of bringing the test coupon in contact with the test water. Examples include: I. a method comprising steps of carrying the test water from pipings of the system to be monitored to a small tank through a branch pipe and then immersing the test coupon into the water (test water) in the tank; II. a method comprising a step of immersing the test coupon into the test water in a bath (e.g. a pit of a cooling tower) disposed in the system to be monitored; III. a method comprising a step of sending the test water from pipings of the system to be monitored to a column through a branch pipe so as to provide the test water flows in the column during the monitoring.

In case of III using water flowing column, it is desirable to use a control valve to make the flow rate in the column constant during the monitoring. In addition, the flow rate of water flowing inside or outside of the piping to be monitored (for example, a piping of a heat exchanger) can be controlled, thereby allowing more precise monitoring.

The method of the present invention can be applied to a corrosion resistance evaluation test in a laboratory for making a determination whether a metallic material can be used in a certain environment or not. In this case, the test coupon made of metallic material to be evaluated and the reference electrode are immersed in aqueous solution, which will be used with the metallic material, in the a vessel (e.g. a beaker) for monitoring.

There is no limitation on the residual stress of the welded portion and the thermal effect (sensitivity) around the welded portion of the test coupon. It is preferable that the test coupon is welded under conditions with the same or slightly higher residual stress and thermal effect as estimated conditions of the metallic materials to be monitored or controlled by heat treatment. This favors the precise prediction about possibility of corrosion of the metallic materials. A plurality of test coupons with various residual stress and thermal effects may be immersed in the solution for monitoring.

There is no particular limitation on the temperature of the heat conductive surface of the test coupon. It is preferable to control the heat transfer surface to have the same or slightly higher temperature as that of the surface temperature of a metal member such as the heat exchanger tubes to be monitored, thereby favoring the precise prediction about possibility of corrosion of the piping to be monitored. A plurality of test coupons having respective heat transfer surfaces under various temperature conditions may be immersed in the solution for monitoring.

The monitoring may be conducted in such a way of immersing a conventional test coupon with uniform metal surface as used in the monitoring of prior art, the conventional test coupon to which a sheet-like heating element is attached to have a heat transfer surface, or the test coupon of the present invention without the heat transfer portion in the test water, and measuring variation the respective corrosion potentials.

The possibility of corrosion of the metallic material within the test water is thus predicted based on the variation pattern in the potential of the test coupon, obtained in the aforementioned manner. The measurement of potential may be entirely conducted by a computer or a data logging equipment. Oxidation-reduction potential may be measured by a platinum electrode, thereby evaluating the oxidizing tendency of the test water at the same time.

EXAMPLE 1

Figure 8:
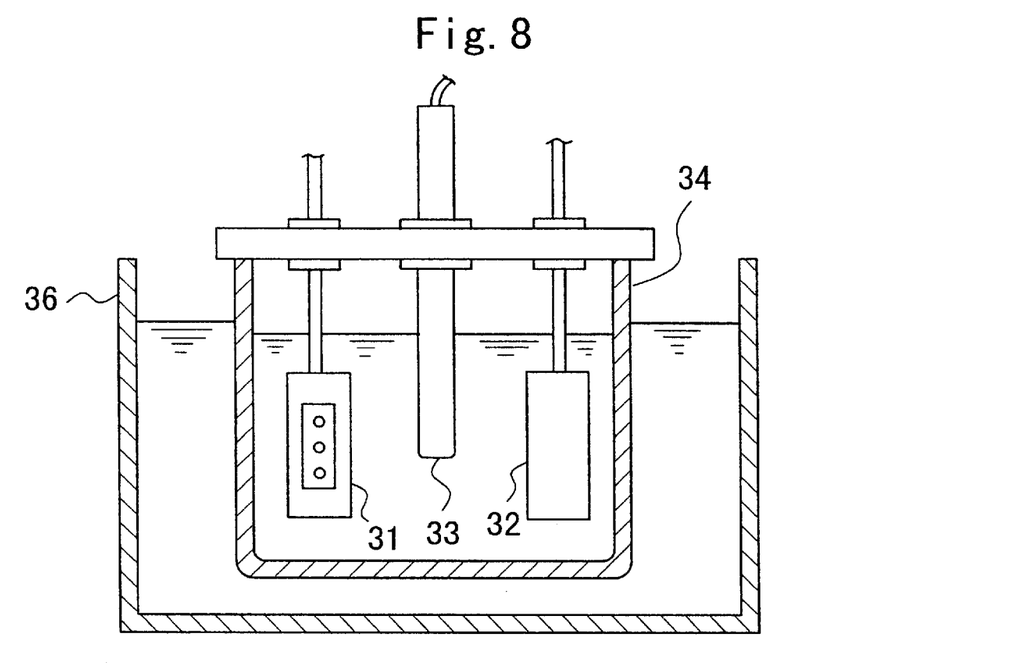
FIG. 8 is an explanatory view illustrating an example of corrosion monitoring method using the test coupon shown in FIGS. 7a through 7d.

The test coupon 31 shown in FIGS. 7a through 7c was used for corrosion monitoring of a metal (SUS304 in this example) by means of a beaker test shown in FIG. 8.

Synthetic cooling water as test water that is simulating cooling water in the actual plant was entered in a beaker of 1 liter and sodium chloride was added in such a manner that the chloride ion concentration in the test water becomes 2000 mg Cl/liter. The main properties of the synthetic cooling water were calcium hardness: 280 mgCaCO$_3$/liter, M alkalinity: 240 mgCaCO$_3$/liter, and magnesium hardness: 160 mgCaCO$_3$/liter. Synthetic polymer for inhibiting scale formation was added in the synthetic cooling water The beaker 34 containing the test water (synthetic cooling water) was entered into a thermobath 36 and was controlled in such a manner the test water is kept at 40° C.

The test coupon 31 of the present invention and a conventional test coupon (SUS304) with uniform metal surface as used in the monitoring of prior art for comparison purpose were immersed in the test water and the potentials were monitored on the basis of the reference electrode (Ag/AgCl/sat. KCl electrode) 33. The temperature of the heat conductive surface of the test coupon 31 of the present invention was set at a temperature of 70° C.

Figure 9:
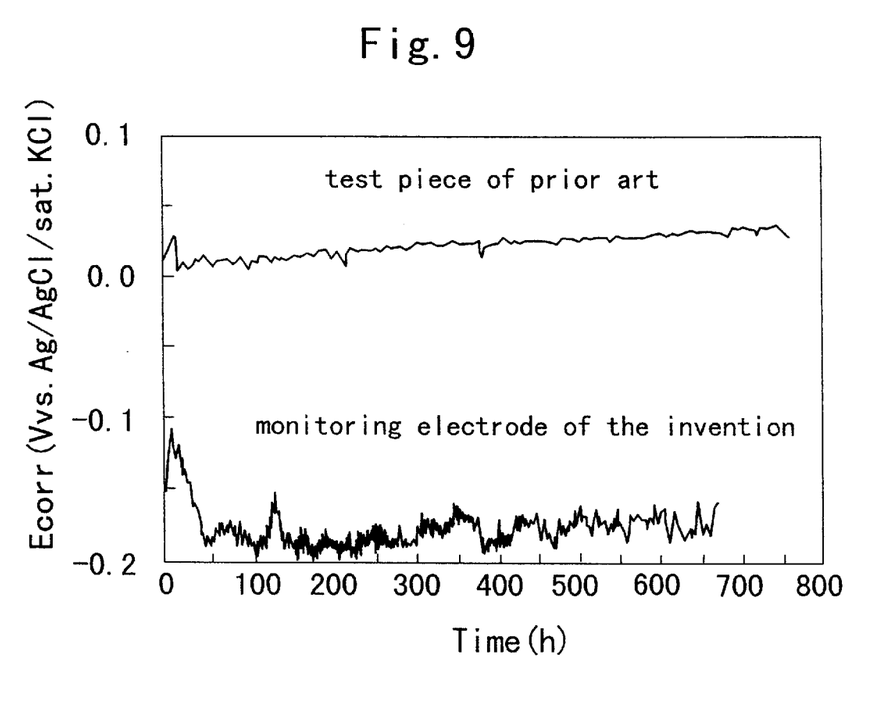
FIG. 9 is a graph showing results of measurement of FIG. 8.

As shown in FIG. 9, the potential of the test coupon of the present invention fell in a short period after the immersion. On the contrary, significant variation in potential of the conventional test coupon 32 was not found during the test.

After the immersion test, the crevice and the portions surrounding the welded portions were observed and, as a result of this, severe crevice corrosion and stress corrosion cracking were found. On the other hand, there was no corrosion on the conventional test coupon 32.

EXAMPLE 2

The test coupon 31 of Example 1 was used in a pilot plant simulating an actual cooling water system for corrosion monitoring of a metal (SUS304 in this example).

Concretely, the test coupon of Example 1 and a conventional test coupon (SUS304) with uniform metal surface as used in the monitoring of prior art for comparison purpose were immersed in water in a pit of a cooling tower. The temperature of the heat conductive surface of the test coupon 31 of the present invention was set at a temperature of 70° C.

Figure 10:
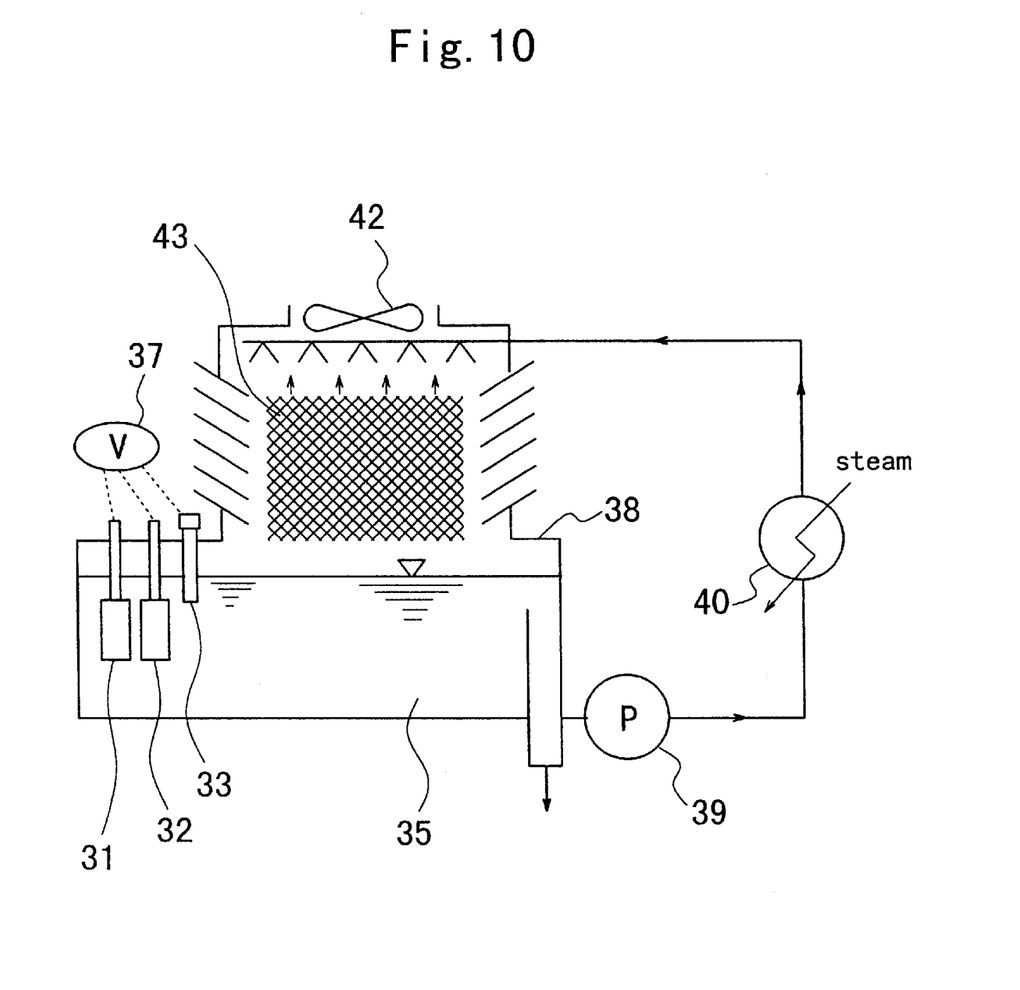
FIG. 10 is a schematic diagram showing a water system of a pilot plant where corrosion monitoring is performed.

The rough arrangement of a test system is shown in FIG. 10. It should be noted that FIG. 10 is a schematic view when the test system is applied to an actual plant. In this system, the recirculating water rate is 340 liters/min, the holding water quantity is 310 liters, the water temperature of cooling water at inlet of a heat exchanger 40 is 30° C., the water temperature for cooling water at outlet a heat exchanger 40 is 40° C. Atsugi-city's service water was used in condensed state as the test water. Suspended solids and deposits in the cooling water system collected from the actual system were added into the test water 35 continuously.

The potentials of the test coupon 31 of the present invention and the conventional test coupon (SUS304) 32 with uniform metal surface as used in the monitoring of prior art were monitored on the basis of the reference electrode (Ag/AgCl/sat. KCl electrode) 33 by a potentiometer 37.

In FIG. 10, the numeral 38 designates a cooling tower pit, 39 designates a conveying pump, 42 designates a fun, and 43 designates filler.

As for the test coupon 31 of the present invention, it was found that foulants were deposited and the crevice had severe crevice corrosion. On the other hand, as for the conventional test coupon 32, dirt was also deposited but in a small amount and severe crevice corrosion was not found.

In the same manner as Example 2, the potential of the test coupon 31 of the present invention fell, while significant variation in potential of the conventional test coupon 32 was not found during the test.

As mentioned above, by using the test coupon of the present invention having welded portion, a crevice, and a heat conductive portion, the monitoring under simulated conditions that the corrosion problem is severe in an actual plant can be realized. Therefore the monitoring according to the present invention has improved sensitivity relative to corrosion reaction as compared to the conventional monitoring. According to the present invention, the prediction about possibility of corrosion on metal materials in an actual plant, that is difficult in the prior art, can be made rapidly and precisely. Therefore, the progress of severe corrosion in the actual plant can be avoided by precaution.

What is claimed is:

1. A corrosion monitoring method for monitoring corrosion of a metal member under heat transfer condition which corrodes in a corrosive fluid, comprising steps of:

heating one substantial surface of a test coupon made of the same material as that of the metal member by a sheet shaped heating element;

bringing at least one portion of the other surface of the test coupon into contact with the corrosive fluid;

detecting a status of corrosion of the test coupon; and monitoring the corrosion of the metal member based on results of the detecting.

2. A corrosion monitoring method as claimed in claim 1, wherein the heating element controls its temperature.

3. A corrosion monitoring method as claimed in claim 2, wherein the heating element comprises a positive temperature coefficient heater.

4. A corrosion monitoring method for monitoring corrosion of a metal member under heat transfer condition which corrodes in a corrosive fluid, comprising steps of:

immersing a counter electrode or a reference electrode in the corrosive fluid, heating one substantial surface of a test coupon made of the same material as that of the metal member by a sheet shaped heating element;

bringing at least one portion of the other surface of the test coupon into contact with the corrosive fluid;

measuring electrical signals between the test coupon and the counter electrode or the reference electrode; and monitoring the corrosion of the metal member based on results of the measurement.

5. A corrosion monitoring apparatus for monitoring corrosion of a metal member under heat transfer condition which corrodes in a corrosive fluid, comprising:

a test coupon made of the same material as that of the metal member;

a sheet shaped heating element for heating one substantial surface of the test coupon; and detecting means for detecting status of corrosion of the test coupon when at least a portion of the other surface of the test coupon is brought in contact with the corrosive fluid.

6. A corrosive monitoring apparatus as claimed in claim 5, further comprising means for controlling temperature of the heating element.

7. A corrosive monitoring apparatus as claimed in claim 6, wherein said means for controlling the temperature of the heating element comprises a positive temperature coefficient heater.

8. A corrosion monitoring apparatus for monitoring corrosion of a metal member under heat transfer condition which corrodes in a corrosive fluid, comprising:

a counter electrode or a reference electrode to be immersed into the corrosive fluid;

a test coupon made of the same material as that of the metal member;

a sheet shaped heating element for heating one substantial surface of the test coupon; and measuring means for measuring electrical signals between the test coupon and the counter electrode or the reference electrode when at least a portion of the other surface of the test coupon is brought in contact with the corrosive fluid.

9. A test coupon for corrosion monitoring of a metal member, wherein the test coupon is made of the same material as that of the metal member under heat transfer condition, and has a welded portion and a crevice.

10. A test coupon for corrosion monitoring as claimed in claim 9, wherein the heat transfer is provided with a sheet shaped heating element attached thereto.

11. A test coupon for corrosion monitoring as claimed in claim 10, wherein said element comprises a positive temperature coefficient heater.

12. A corrosion monitoring method using a test coupon as claimed in claim 9 to measure variation in corrosion potential of the test coupon.

13. A corrosion monitoring apparatus comprising a test coupon as claimed in claim 9 and means for measuring variation in potential of corrosion of the test coupon.

14. A corrosion monitoring apparatus as claimed in claim 13, wherein said test coupon comprises a positive temperature coefficient heater.

* * * * *